United States Patent [19]
Waldmann et al.

[11] 3,933,910
[45] Jan. 20, 1976

[54] PROCESS FOR THE PRODUCTION OF KETAZINES

[75] Inventors: Helmut Waldmann, Leverkusen; Hermann Seifer, Cologne; Wulf Schwerdtel, Leverkusen; Wolfgang Swodenk, Odenthal-Gloebusch; Kurt-Wilheim Eichenhofer, Leverkusen, all of Germany

[73] Assignee: Bayer Aktiengesellschaft, Leverkusen, Germany

[22] Filed: May 14, 1974

[21] Appl. No.: 469,939

[30] Foreign Application Priority Data
May 19, 1973 Germany............................ 2325460

[52] U.S. Cl...... 260/561 A; 260/557 R; 260/562 N; 260/566 B
[51] Int. Cl.²....................................... C07C 119/00
[58] Field of Search ........ 260/566 B, 557 R, 562 N, 260/561 A

[56] References Cited
OTHER PUBLICATIONS
German Offenlegungsschrift 2,143,516 (7-20-72).

Primary Examiner—Gerald A. Schwartz
Attorney, Agent, or Firm—Burgess, Dinklage & Sprung

[57] ABSTRACT

A process for the production of ketazine corresponding to the general formula

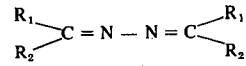

in which:
$R_1$ and $R_2$ are independently linear or branched alkyl radicals of from 1 to 8 carbon atoms or a phenyl radical, or taken together with the carbon atom to which they are attached represent a carbocyclic ring with 5 to 8 carbon atoms or a cyclic alkyl radical with 5 to 8 carbon atoms, comprising reacting ammonia, hydrogen peroxide and a ketone of the general formula
$R_1 - CO - R_2$
in which $R_1$ and $R_2$ are as defined above, in the presence of hydrocyanic acid.

8 Claims, No Drawings

PROCESS FOR THE PRODUCTION OF KETAZINES

This invention relates to a new process for the production of ketazines.

Processes for the production of ketazines are known. According to German Offenlegungsschrift 2,143,516 for example, ammonia, hydrogen peroxide, a ketone and a nitrile are reacted to form particular ketazines together with the acid amide corresponding to the nitrile used and other secondary products. One major disadvantage of this process is that the corresponding acid amide formed as the secondary product from the nitrile is undesirable.

It has now been found that ketazines corresponding to the general formula

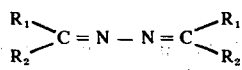

in which:

$R_1$ and $R_2$ are independently linear or branched alkyl radicals of from 1 to 8 carbon atoms such as methyl or ethyl, which may optionally be attached to form a carbocyclic ring with 5 to 8 ring carbon atoms or a cyclic alkyl radical with 5 to 8 carbon atoms or a phenyl radical can be obtained by reacting ammonia, hydrogen peroxide and a ketone of the general formula $R_1$-CO-$R_2$, in which $R_1$ and $R_2$ are as defined above, by an improved process which is distinguished by the fact that the reaction is carried out in the presence of hydrocyanic acid.

The ammonia which is used as the starting product may be liquid or gaseous. The hydrogen peroxide may be used either in an aqueous or a non-aqueous solution of any concentration. Among the non-aqueous solvents, phosphonic acid esters, phosphoric acid esters, N-methyl pyrrolidone or $C_4$-$C_6$-alkyl acetic acid esters or $C_4$-$C_6$-alkyl propionic acid esters, have proved to be of particular advantage. In general, the hydrogen peroxide is used in the form of a 30 to 90 percent weight aqueous solution and preferably in the form of a 50 to 70 percent by weight aqueous solution.

The ketones may be symmetrical or asymmetrical, preferably those of the kind whose radicals $R_1$ and $R_2$ do not sterically hinder the carbonyl group. The following ketones are mentioned by way of example: acetone, butanone, 2-pentanone, 3-pentanone, methyl isopropylketone, methyl isobutylketone, methyl cyclohexylketone, dicyclohexylketone, 2-hexanone, 3-hexanone, 2-heptanone, benzophenone, cyclopentanone, cyclohexanone and cycloheptanone. Acetone and butanone are particularly preferred.

The process according to the invention is generally carried out at temperatures of from −20° to +100°C, and preferably at temperatures of from 0°C to +50°C.

The pressure applied in the process according to the invention is not a critical parameter. The reaction is generally carried out under atmospheric pressure, although in some cases it has proved to be of advantage to carry out the reaction at an elevated pressure, for example under pressures of from 2 to 10 bars, in order to increase the concentration of the volatile reaction components present in the reaction mixture.

The molar ratios of the reactants can vary within wide limits. In general, ketone and ammonia are both reacted in quantities of from 1 to 10 moles, preferably in quantities of from 2 to 4 moles, per mole of hydrogen peroxide.

The hydrocyanic acid used for the reaction can be used in equimolecular quantities, based on hydrogen peroxide. Particularly good results are obtained where approximately 2 to 4 moles of hydrocyanic acid are used per mole of hydrogen peroxide.

The reaction can be carried out in the presence or absence of solvents. In general, it has proved to be of advantage to carry out the reaction in an alcoholic reaction medium, for example in methanol, ethanol or isopropanol.

In practice, the process according to the invention can be carried out for example by initially introducing ketone and hydrogen peroxide and successively adding ammonia and hydrocyanic acid. However, it is also possible to initially introduce the ketone and hydrocyanic acid and then successively to add ammonia and hydrogen peroxide.

The individual reaction components can of course also be reacted with one another beforehand to form defined intermediate products, for example ketone peroxides or amino peroxides of the ketones, and the intermediate products thus formed may be used in the reaction.

The reaction mixture is sensitive to decomposition catalysts for peroxides, so that it is best to stabilize them with peroxide stabilizers known per se, for example the sodium salt of ethylenediamine tetracetic acid or sodium phosphates.

The process according to the invention does not impose any particular requirements upon the type of reaction vessel used and, in view of the presence of hydrogen peroxide in the reaction mixture, can be carried out for example in stirrer-equipped vessels, bubble reactors, residence-time tubes or the like. The reaction vessel used is preferably made of such materials as, for example, enamels, Cr-Ni fine steels or passivated aluminum.

The reaction may be carried out continuously or in batches. The process is eminently suitable for large-scale working, because all the unreacted fractions can be recycled without any losses.

The ketazines obtained by the process according to the invention are important intermediate products which can be hydrolyzed by methods known per se to form hydrazine in the form of the free base or in the form of a salt of hydrazine.

The mixture is worked up by methods known per se. The azines can be isolated by, for example distillation or extraction. It is also possible, however, to further react the reaction mixture without prepurifying to form a hydrazine.

The process according to the invention is of particular value because the required ketazines are obtained in a yield of up to 90 percent, based on hydrogen peroxide. Depending upon the reaction conditions, the corresponding hydrazine is formed as a derivative product in a yield of from 0 to 30 percent in competition with the ketazines, although this is by no means a disadvantage in view of the use of the reaction product obtained by the process according to the invention for the production of hydrazine, because both products give substantially quantitative yields of hydrazine as hydrolysis product.

α-Amino carboxylic acid amides are simultaneously formed as co-products in the process according to the invention. These amides contain the radicals $R_1$ and $R_2$ of the ketone which was used for the reaction, on the a-carbon.

α-Amino carboxylic acid amides are valuable intermediate products because they can be transformed in known manner to form the corresponding α,β-unsaturated carboxylic acid amides. α,β-unsaturated carboxylic acid amides are valuable components in copolymers (Ullmans Enzyklopadie der techn. Chemie 1960, Vol. 12, pages 391 – 397).

Accordingly, the advanced nature of the process according to the invention is embodied in the fact that, by comparison with conventional process, hydrazine can be obtained by way of the ketazines in high yields, based on the hydrogen peroxide used.

Further particular advantages are the fact that hydrocyanic acid can be used as an inexpensive starting component and the fact that the extremely valuable intermediate products, α-amino carboxylic acids and the corresponding α,β-unsaturated carboxylic acid amides, which can readily be separated off from the reaction mixture, are formed instead of undesirable secondary products.

The invention is illustrated by the following examples:

EXAMPLE 1

$NH_3$-gas was introduced up to saturation into a mixture of 58 g (1 mole) of acetone, 7.2 g (0.15 mole) of 70 percent by weight aqueous hydrogen peroxide, 0.2 g of the sodium salt of ethylenediamine tetracetic acid and 24 g of methanol, which had been cooled with ice water to 13°C. 10 g of anhydrous hydrocyanic acid was then added dropwise over a period of 10 minutes. The reaction mixture thus obtained was heated to +40°C over a period of 30 minutes and stirred at that temperature for another 2 hours.

The reaction mixture obtained contained 11.5 g of acetoneazine and 2.5 g of acetonehydrazone (according to analysis by gas chromatography). In addition, it was found to contain 10 g of a mixture of α-amino isobutyric acid amide and methacryl-amide. The acetone azine was identified from the NMR-spectrum after working up by distillation. The selectivity for acetoneazine amounted to 68.3 percent and for acetone hydrazone to 23.1 percent, based on $H_2O_2$ used.

Accordingly, the overall selectivity for hydrazine derivatives amounted to 91.4 percent, based on $H_2O_2$ used.

EXAMPLE 2

4 g (0.147 mole) HCN were added to a mixture of 80 ml of methanol, 26.5 g (0.457 mole) of acetone and 18 g of water. A vigorous stream of ammonia was then introduced at room temperature up to the saturation point. The mixture was then heated to 45°C, followed by the addition, over a period of 15 minutes, of 7.15 g. (0.147 mole) of 70 percent aqueous hydrogen peroxide. The reaction mixture underwent a spontaneous increase in temperature to 54°C. The reaction mixture was then kept at 55° to 60°C for another 2 hours, during which more ammonia was introduced. 10.86 g of acetone azine and 1.45 g of acetone hydrazone were obtained, corresponding to 96.2 percent of the hydrogen peroxide reacting. The selectivity for ketazine amounts to 68.5 percent and for hydrazone to 14.2 percent, based on $H_2O_2$ reacted.

In addition, 4.68 g (0.0454 mole) of α-amino isobutyramide and 4.9 g (0.0576 mole) of methacrylamide were formed. This corresponds to a selectivity for these two products of 70.1 percent, based on the acetone used.

What is claimed is:

1. In the production of a ketazine corresponding to the general formula

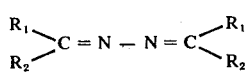

in which
R₁ and R₂ are independently linear or branched alkyl radicals of from 1 to 8 carbon atoms, a phenyl radical, a cyclic alkyl radical with 5 to 8 carbon atoms, or taken together with the carbon atoms to which they are attached represent a carbocyclic ring with 5 to 8 carbon atoms, by reacting ammonia, hydrogen peroxide, a -CN containing compound and a ketone of the general formula

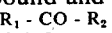

in which R₁ and R₂ are as defined above, the improvement which comprises using hydrocyanic acid as said -CN containing compound and effecting said reaction at from -20°C to 100°C, whereby said ketazine is produced along with an α-amino carboxylic acid amide of the formula

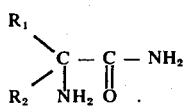

2. A process as claimed in claim 1, in which R₁ and R₂ are selected from the group consisting of methyl and ethyl radicals.

3. A process as claimed in claim 1, in which the ketone is at least one ketone selected from the group consisting of acetone and butanone.

4. A process as claimed in claim 1, comprising adjusting the temperature from about 0°C to 50°C.

5. A process as claimed in claim 1, comprising using 1 to 10 moles of ketone, 1 to 10 moles of ammonia and 1 to 4 moles of hydrocyanic acid per mole of hydrogen peroxide.

6. A process as claimed in claim 5, comprising using from 2 to 4 moles of each of the ketone, ammonia and hydrocyanic acid per mole of hydrogen peroxide.

7. A process as claimed in claim 1, comprising using hydrogen peroxide and ketone in the form of ketone peroxides.

8. A process as claimed in claim 1, comprising using ammonia, ketones and hydrogen peroxide in the form of ketone aminoperoxides.

* * * * *

UNITED STATES PATENT AND TRADEMARK OFFICE
CERTIFICATE OF CORRECTION

PATENT NO. : 3,933,910
DATED : January 20, 1976
INVENTOR(S) : Helmut Waldmann et al It is certified that error appears in the above-identified patent and that said Letters Patent are hereby corrected as shown below:

Page 1, item [75] "Inventors:" correct spelling of name of second inventor -- Seifert --.

Signed and Sealed this eighteenth Day of May 1976

[SEAL]

Attest:

RUTH C. MASON
Attesting Officer

C. MARSHALL DANN
Commissioner of Patents and Trademarks